US008491497B2

(12) United States Patent
Houser et al.

(10) Patent No.: US 8,491,497 B2
(45) Date of Patent: Jul. 23, 2013

(54) METHOD AND APPARATUS FOR MORCELLATING TISSUE

(75) Inventors: Kevin L. Houser, Springboro, OH (US); Robert E. Sackett, Maineville, OH (US); Edward G. Chekan, Cincinnati, OH (US); Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 289 days.

(21) Appl. No.: 12/779,155

(22) Filed: May 13, 2010

(65) Prior Publication Data
US 2011/0282238 A1 Nov. 17, 2011

(51) Int. Cl.
*A61B 10/02* (2006.01)
(52) U.S. Cl.
USPC ............ 600/568; 600/562; 600/564; 241/69; 241/70; 241/71
(58) Field of Classification Search
USPC ................... 241/69–71; 600/562, 564, 568
See application file for complete search history.

(56) References Cited

U.S. PATENT DOCUMENTS

| | | | | |
|---|---|---|---|---|
| 3,298,411 A | * | 1/1967 | Rosett | 241/84.1 |
| 3,666,187 A | * | 5/1972 | Norris | 241/89.4 |
| 5,267,955 A | * | 12/1993 | Hanson | 604/22 |
| 5,526,822 A | | 6/1996 | Burbank et al. | |
| 5,694,951 A | | 12/1997 | Bonutti | |
| 5,817,032 A | * | 10/1998 | Williamson et al. | 600/562 |
| 6,086,544 A | | 7/2000 | Hibner et al. | |
| 6,990,982 B1 | | 1/2006 | Bonutti | |
| 7,115,100 B2 | | 10/2006 | McRury et al. | |
| 7,156,814 B1 | * | 1/2007 | Williamson et al. | 600/562 |
| 7,270,284 B2 | * | 9/2007 | Liao et al. | 241/69 |
| 7,442,171 B2 | | 10/2008 | Stephens et al. | |
| 7,611,473 B2 | | 11/2009 | Boock et al. | |
| 7,686,770 B2 | * | 3/2010 | Cohen | 600/568 |
| 7,998,086 B2 | * | 8/2011 | Boock et al. | 600/566 |
| 8,034,003 B2 | * | 10/2011 | Pesce et al. | 600/564 |
| 8,286,899 B2 | * | 10/2012 | Schowalter et al. | 241/2 |

(Continued)

FOREIGN PATENT DOCUMENTS

GB   237452   7/1925

OTHER PUBLICATIONS

U.S. Appl. No. 12/483,305, filed Jun. 12, 2009, Hibner et al.

(Continued)

*Primary Examiner* — Sean Dougherty
(74) *Attorney, Agent, or Firm* — Frost Brown Todd LLC

(57) ABSTRACT

An apparatus for morcellating tissue specimens comprises a housing and a cutting member. The cutting member is operable to cut tissue specimens into morcellated or minced tissue pieces. The cutting member may include one or more screens. One of the screens may be rotatable or capable of reciprocating relative to the housing. One screen may cooperate with another screen to provide shearing of the tissue specimens. The cutting member may include a plurality of discs that are rotatable relative to the housing. The discs may include inwardly directed notches formed in their outer perimeter, with the notches cooperating with an interior wall of the housing to cut tissue specimens. The discs may include perimeters having ovular or elliptical shapes that cooperate with a cylindrical interior wall of the housing to cut tissue specimens. The apparatus may be a stand-alone apparatus or may be incorporated into a tissue harvesting apparatus.

7 Claims, 9 Drawing Sheets

U.S. PATENT DOCUMENTS

| | | |
|---|---|---|
| 2004/0078090 A1 | 4/2004 | Binette et al. |
| 2004/0158226 A1* | 8/2004 | Soo Hoo et al. ............... 604/500 |
| 2004/0193071 A1 | 9/2004 | Binette et al. |
| 2005/0038520 A1 | 2/2005 | Binette et al. |
| 2005/0059905 A1* | 3/2005 | Boock et al. ................... 600/567 |
| 2005/0113736 A1 | 5/2005 | Orr et al. |
| 2005/0125077 A1 | 6/2005 | Harmon et al. |
| 2005/0165329 A1* | 7/2005 | Taylor et al. .................. 600/566 |
| 2006/0122641 A1* | 6/2006 | Eberle et al. ................... 606/184 |
| 2007/0149990 A1* | 6/2007 | Palmer et al. .................. 606/167 |
| 2008/0035767 A1* | 2/2008 | Schmid et al. ............. 241/24.26 |
| 2008/0071385 A1 | 3/2008 | Binette et al. |
| 2008/0214955 A1 | 9/2008 | Speeg et al. |
| 2008/0234602 A1* | 9/2008 | Oostman et al. ............... 600/564 |
| 2008/0234715 A1 | 9/2008 | Pesce et al. |
| 2008/0311219 A1 | 12/2008 | Gosiewska et al. |
| 2009/0112119 A1* | 4/2009 | Kim ................................ 600/564 |
| 2010/0160819 A1 | 6/2010 | Parihar et al. |
| 2010/0210967 A1* | 8/2010 | Sjunnesson et al. .......... 600/567 |
| 2011/0282372 A1* | 11/2011 | Schowalter et al. .......... 606/170 |

OTHER PUBLICATIONS

International Search Report dated Sep. 1, 2011 for Application No. PCT/US2011/036442.

* cited by examiner

METHOD AND APPARATUS FOR MORCELLATING TISSUE

BACKGROUND

Fistulae can occur for a variety of reasons, such as, from a congenital defect, as a result of inflammatory bowel disease such as Crohn's disease, some sort of trauma, or as a side effect from a surgical procedure. Additionally, several different types of fistulae can occur in humans, for example, urethro-vaginal fistulae, vesico-vaginal fistulae, tracheo-esophageal fistulae, gastrointestinal fistulae, for example gastrocutaneous, enterocutaneous and colocutaneous fistulae, and any number of anorectal fistulae such as recto-vaginal fistula, recto-vesical fistulae, recto-urethral fistulae, and recto-prostatic fistulae. When fistulas form, they can track between intestinal segments or between an intestinal segment and other organs (e.g., bladder, vagina, etc.), adjacent tissue, or the skin. Fistulas are classified as internal when they communicate with adjacent organs (e.g., entero-enteric and rectovaginal fistulas, etc.) and external when they communicate with the dermal surface (e.g., enterocutaneous, peristomal and perianal fistulas, etc.).

Promoting and improving tissue healing around the fistula opening and in the fistula tract may be an important aspect of fistulae medical treatments. For instance, promoting and improving tissue healing may lead to quicker recovery times and lessen the opportunity for infection, particularly in a post-surgical context. Some advancements in the medical arts pertaining to systems, methods, and devices to promote and improve tissue healing in patients aim to add active biological components (e.g., tissue particles, stem cells, other types of cells, etc.) to a wound site (e.g., surgical site, accidental trauma site, etc.) or other defect site (e.g., caused by disease or other condition, etc.) to promote tissue regeneration or accelerate tissue healing. When adding biological components to a site, such components may be added independently or as part of a specifically designed matrix or other mixture depending on the condition being treated and goals of the treatment. Some examples of cell-based therapy technology are disclosed in U.S. Pub. No. 2008/0311219, entitled "Tissue Fragment Compositions for the Treatment of Incontinence," published Dec. 18, 2008, the disclosure of which is incorporated by reference herein. Additional examples of cell-based therapy technology are disclosed in U.S. Pub. No. 2004/0078090, entitled "Biocompatible Scaffolds with Tissue Fragments," published Apr. 22, 2004, the disclosure of which is incorporated by reference herein. Additional examples of cell-based therapy technology are disclosed in U.S. Pub. No. 2008/0071385, entitled "Conformable Tissue Repair Implant Capable of Injection Delivery," published Mar. 20, 2008, and issued Jan. 25, 2011 as U.S. Pat. No. 7,875,296, the disclosure of which is incorporated by reference herein.

Regardless of how the active biological components are delivered or applied to a site, the biological components must first be obtained and prepared. One approach for obtaining such biological components is to harvest the desired components from a healthy tissue specimen (e.g., in an adult human). Examples of devices and associated methods for collecting and processing harvested tissue are disclosed in U.S. Pub. No. 2004/0193071, and issued Sep. 14, 2010 as U.S. Pat. No. 7,794,408, entitled "Tissue Collection Device and Methods," published Sep. 30, 2004, the disclosure of which is incorporated by reference herein. Additional examples of devices and associated methods for collecting and processing harvested tissue are disclosed in U.S. Pub. No. 2005/0038520, entitled "Method and Apparatus for Resurfacing an Articular Surface," published Feb. 17, 2005, the disclosure of which is incorporated by reference herein. Additional examples of devices and associated methods for collecting and processing harvested tissue are disclosed in U.S. Pat. No. 7,611,473, entitled "Tissue Extraction and Maceration Device," issued Nov. 3, 2009, the disclosure of which is incorporated by reference herein. Additional examples of devices and associated methods for collecting and processing harvested tissue are disclosed in U.S. Pub. No. 2008/0234715, entitled "Tissue Extraction and Collection Device," published Sep. 25, 2008, and issued Oct. 11, 2011 as U.S. Pat. No. 8,034,003, the disclosure of which is incorporated by reference herein. Additional examples of devices and associated methods for processing harvested tissue are disclosed in U.S. Pub. No. 2005/0125077, entitled "Viable Tissue Repair Implants and Methods of Use," published Jun. 9, 2005, and issued Mar. 8, 2011 as U.S. Pat. No. 7,901,461, the disclosure of which is incorporated by reference herein. Additional examples of devices and associated methods for collecting and processing harvested tissue are disclosed in U.S. Pat. No. 5,694,951, entitled "Method for Tissue Removal and Transplantation," issued Dec. 9, 1997, the disclosure of which is incorporated by reference herein. Additional examples of devices and associated methods for collecting and processing harvested tissue are disclosed in U.S. Pat. No. 6,990,982, entitled "Method for Harvesting and Processing Cells from Tissue Fragments," issued Jan. 31, 2006, the disclosure of which is incorporated by reference herein. Additional examples of devices and associated methods for collecting and processing harvested tissue are disclosed in U.S. Pat. No. 7,115,100, entitled "Tissue Biopsy and Processing Device," issued Oct. 3, 2006, the disclosure of which is incorporated by reference herein.

Once harvested and suitably processed (e.g., incorporated with a scaffold, etc.), biological material such as tissue fragments may be applied to a wound site or other type of site within the human body in a variety of ways. Various methods and devices for applying such biological material are disclosed in one or more of the U.S. patent references cited above. Additional methods and devices for applying such biological material are disclosed in U.S. Pub. No. 2005/0113736, entitled "Arthroscopic Tissue Scaffold Delivery Device," published May 26, 2005, the disclosure of which is incorporated by reference herein.

While a variety of devices and techniques may exist for harvesting, processing, and applying biological components from a tissue specimen, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings. In the drawings, like numerals represent like elements throughout the several views.

Figure 1:
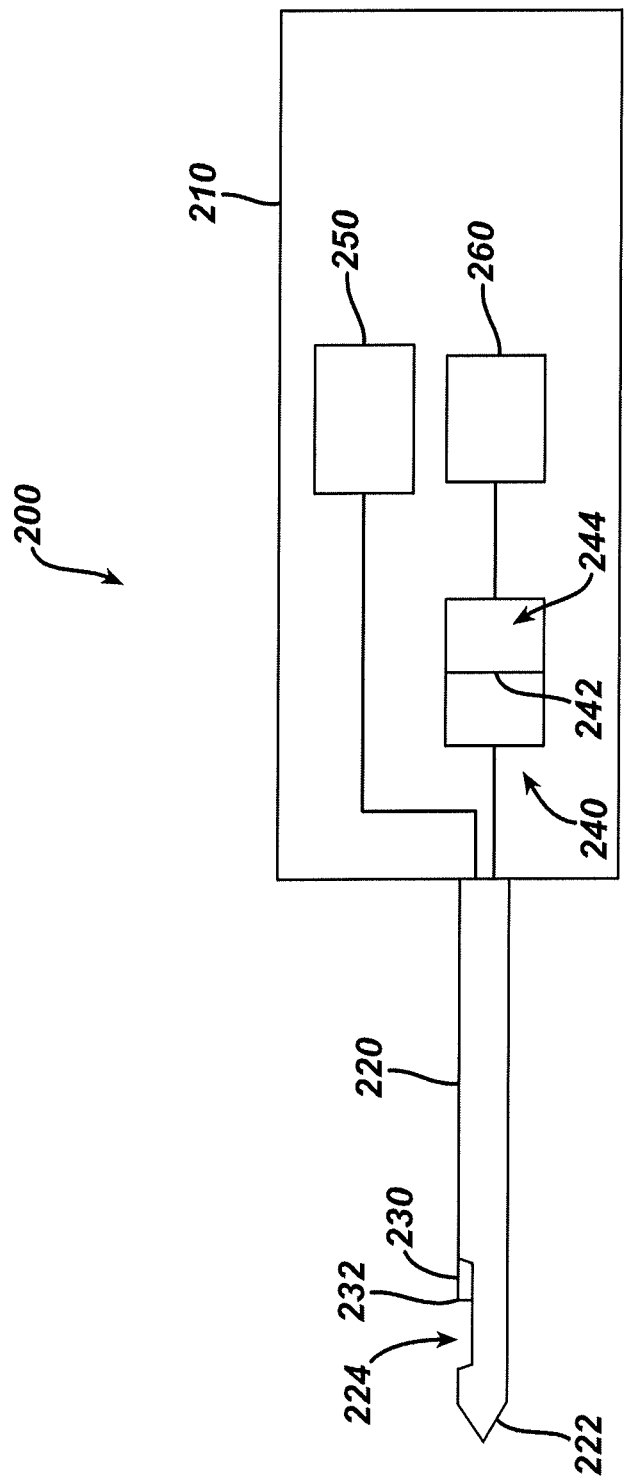
FIG. 1 depicts a system schematic view of an exemplary tissue harvesting and morcellating system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

I. Overview of Exemplary Treatment Compositions, Devices, and Methods

Examples described herein include devices that are operable to harvest tissue, mince or morcellate tissue, and/or mix tissue particles with other medical fluid components, such as for dispensation at a target site in a patient. As described in greater detail below, the medical fluid may include any of a variety of biocompatible materials that accelerate tissue healing, promote tissue regeneration, and/or provide other results. As used herein, the terms "tissue treatment composition," "tissue repair composition," and "medical fluid" should be read interchangeably. It should also be understood that a tissue treatment composition or medical fluid as referred to herein may have any suitable consistency, including but not limited to the consistency of a slurry.

A medical fluid as referred to herein may be derived from any biocompatible material, including but not limited to synthetic or natural polymers. The consistency of the medical fluid may be viscous, or gel-like, that of a slurry composed of microparticles, or any other suitable consistency. By way of example only, any fluid consistency that may permit injection through a catheter may be used. The medical fluid may also provide adhesive characteristics, such that once it is injected at a target site (e.g., into a fistula), the fluid coagulates or gels (e.g., allowing for a plug to be retained within a fistula). The medical fluid of the present example is also able to support cell migration and proliferation such that healing at a target site in a patient can occur. The fluid is suitable to be mixed with biological materials. Examples of medical fluid components include but are not limited to thrombin, platelet poor plasma (PPP) platelet rich plasma (PRP), starch, chitosan, alginate, fibrin, polysaccharide, cellulose, collagen, gelatin-resorcin-formalin adhesive, oxidized cellulose, mussel-based adhesive, poly (amino acid), agarose, amylose, hyaluronan, polyhydroxybutyrate (PHB), hyaluronic acid, poly(vinyl pyrrolidone) (PVP), poly(vinyl alcohol) (PVA), polylactide (PLA), polyglycolide (PGA), polycaprolactone (PCL), and their copolymers, VICRYL® (Ethicon, Inc., Somerville, N.J.), MONOCRYL material, PANACRYL (Ethicon, Inc., Somerville, N.J.), and/or any other material suitable to be mixed with biological material and introduced to a wound or defect site, including combinations of materials. Other suitable compounds, materials, substances, etc., that may be used in a medical fluid will be apparent to those of ordinary skill in the art in view of the teachings herein.

By way of example only, one or more components in a medical fluid or tissue treatment composition may comprise at least one viable tissue fragment having one or more viable cells that, once applied, can proliferate and integrate with tissue at a target site in a patient. For instance, viable cells may migrate out of a tissue particle and populate a scaffold material, which may be positioned at a target site in a patient. Such tissue fragments may have been harvested from the same patient in whom they are reapplied; or may have been harvested from another person or source. The tissue fragments may comprise autogenic tissue, allogenic tissue, xenogenic tissue, mixtures of any of the foregoing, and/or any other type(s) of tissue. The tissue fragments may include, for example, one or more of the following tissues or tissue components: stem cells, cartilage tissue, meniscal tissue, ligament tissue, tendon tissue, skin tissue, muscle tissue (e.g., from the patient's thigh, etc.), periosteal tissue, pericardial tissue, synovial tissue, fat tissue, bone marrow, bladder tissue, umbilical tissue, embryonic tissue, vascular tissue, blood and combinations thereof. Of course, any other suitable type of tissue may be used, including any suitable combination of tissue types. In some versions, the type of tissue used is selected from a tissue type most resembling the tissue at, near, or surrounding the target site (e.g., fistula, etc.).

Tissue for providing at least one viable tissue fragment may be obtained using any of a variety of tissue biopsy devices or using other types of tissue harvesting devices or techniques. Exemplary biopsy devices include those taught in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2007/0118048, entitled "Remote Thumbwheel for a Surgical Biopsy Device," published May 24, 2007, and issued Oct. 28, 2008 as U.S. Pat. No. 7,442,171; U.S. Pub. No. 2008/0214955, entitled "Presentation of Biopsy Sample by Biopsy Device," published Sep. 4, 2008; U.S. Non-Provisional patent application Ser. No. 12/337,942, entitled "Biopsy Device with Central Thumbwheel," filed Dec. 18, 2008, and published Jun. 24, 2010 as U.S. Pub. No. 2010/0160819; and U.S. Non-Provisional patent application Ser. No. 12/483,305, entitled "Tetherless Biopsy Device with Reusable Portion," filed Jun. 12, 2009, and issued Jun. 26, 2012 as U.S. Pat. No. 8,206,316. The disclosure of each of the above-cited U.S. patents, U.S. Patent Application Publications, and U.S. Non-Provisional Patent Applications is incorporated by reference herein. Such biopsy devices may be used to extract a plurality of tissue specimens from one or more sites in a single patient. It should also be understood that any suitable device described in any other reference that is cited herein may be used to harvest tissue. Additional examples of devices that may be used to harvest tissue will be described in greater detail below. Other examples will be apparent to those of ordinary skill in the art in view of the teachings herein. Tissue harvesting sites may include the same sites in which tissue is reapplied as part of a treatment. In addition or in the alternative, tissue may be harvested from one site and then reapplied at some other site as part of a treatment. In some versions, the tissue is reapplied in the same patient from whom the tissue was originally harvested. In some other versions, the tissue is applied in a patient who is different from the patient from whom the tissue was originally harvested.

A tissue specimen may be obtained under aseptic conditions, and then processed under sterile conditions to create a suspension having at least one minced, or finely divided, tissue fragment. In other words, harvested tissue may be diced, minced or morcellated, and/or otherwise processed. Harvested tissue specimens may be minced and otherwise processed in any of a variety of ways. For instance, examples of tissue mincing and processing are described in U.S. Pub. No. 2004/0078090, the disclosure of which is incorporated by reference herein. Alternatively, merely exemplary non-conventional devices and techniques that may be used to mince and process tissue will be described in greater detail below, while other examples will be apparent to those of ordinary skill in the art in view of the teachings herein. In order to ensure viability of the tissue, agitators or other features of a mincing and/or mixing device may be designed to sever and mix (rather than crush or compress) the tissue. In some settings, tissue specimens may be minced and/or mixed in a standard cell culture medium, either in the presence or absence of serum. Tissue fragments may also be contacted with a matrix-digesting enzyme to facilitate cell migration out of an extracellular matrix surrounding the cells. Suitable matrix-digesting enzymes that may be used in some settings include, but are not limited to, collagenase, chondroitinase, trypsin, elastase, hyaluronidase, peptidase, thermolysin, and protease. The size of each tissue fragment may vary depending on the target location, method for delivering the treatment composition to the target site, and/or based on various other considerations. For example, the tissue fragment size may be chosen to enhance the ability of regenerative cells (e.g., fibroblasts) in the tissue fragments to migrate out of the tissue fragments, and/or to limit or prevent the destruction of cell integrity. In some settings, ideal tissue fragments are between approximately 200 microns and approximately 500 microns in size. As another merely illustrative example, ideal tissue fragments may be sized within the range of approximately 0.05 mm$^3$ and approximately 2 mm$^3$; or more particularly between approximately 0.05 mm$^3$ and approximately 1 mm$^3$. Of course, various other tissue fragment sizes may be ideal in various different settings.

In some versions, a medical fluid may comprise minced tissue fragments suspended in a biocompatible carrier. Suitable carriers may include, for example, a physiological buffer solution, a flowable gel solution, saline, and water. In the case of gel solutions, the tissue repair composition may be in a flowable gel form prior to delivery at the target site, or may form a gel and remain in place after delivery at the target site. Flowable gel solutions may comprise one or more gelling materials with or without added water, saline, or a physiological buffer solution. Suitable gelling materials include biological and synthetic materials. Exemplary gelling materials include the following: proteins such as collagen, collagen gel, elastin, thrombin, fibronectin, gelatin, fibrin, tropoelastin, polypeptides, laminin, proteoglycans, fibrin glue, fibrin clot, platelet rich plasma (PRP) clot, platelet poor plasma (PPP) clot, self-assembling peptide hydrogels, Matrigel or atelocollagen; polysaccharides such as pectin, cellulose, oxidized regenerated cellulose, chitin, chitosan, agarose, or hyaluronic acid; polynucleotides such as ribonucleic acids or deoxyribonucleic acids; other materials such as alginate, cross-linked alginate, poly(N-isopropylacrylamide), poly(oxyalkylene), copolymers of poly(ethylene oxide)-polypropylene oxide), poly(vinyl alcohol), polyacrylate, or monostearoyl glycerol co-Succinate/polyethylene glycol (MGSA/PEG) copolymers; and combinations of any of the foregoing. In addition to providing a flowable carrier solution for tissue fragments, a gelling agent(s) may also act as an adhesive that anchors the tissue repair composition at the target site. In some versions, an additional adhesive anchoring agent may be included in the tissue repair composition or medical fluid. Also, one or more cross-linking agents may be used in conjunction with one or more gelling agents in order to cross-link the gelling agent.

The concentration of tissue fragments in a carrier and/or one or more medical fluid components may vary depending on the target site location, method for delivering the treatment composition to the target site, and/or for various other reasons. By way of example, the ratio of tissue fragments to carrier (by volume) may be in the range of about 2:1 to about 6:1, or in the range of about 2:1 to about 3:1. The medical fluid may also include one more additional healing agents, such as biological components that accelerate healing and/or tissue regeneration. Such biological components may include, for example, growth factors, proteins, peptides, antibodies, enzymes, platelets, glycoproteins, hormones, cytokines, glycosaminoglycans, nucleic acids, analgesics, viruses, isolated cells, or combinations thereof. The medical fluid may further include one or more additional treatment components that prevent infection, reduce inflammation, prevent or minimize adhesion formation, and/or suppress the immune system. In some versions where a scaffold is used in conjunction with a tissue treatment composition, one or more of these additional biological components or additional treatment components may be provided on and/or within the scaffold. Similarly, in some versions where a scaffold plug is used in conjunction with a tissue repair composition, one or more of these additional biological components or additional treatment components may be provided on and/or within the scaffold plug. Some examples described herein may also include one or more adhesive agents in conjunction with viable tissue fragments.

As noted above, the harvested tissue may be combined with a scaffold material and/or other substances as part of a medical fluid, as described herein, for administration to the patient. To the extent that tissue is incorporated with a scaffold material, it should be understood that any suitable material or combination of materials may be used to provide a scaffold. By way of example only, scaffold material may include a natural material, a synthetic material, a bioabsorbable polymer, a non-woven polymer, other types of polymers, and/or other types of materials or combinations of materials. Examples of suitable biocompatible materials include starch, chitosan, cellulose, agarose, amylose, lignin, hyaluronan, alginate, hyaluronic acid, fibrin glue, fibrin clot, collagen gel, gelatin-resorcin-formalin adhesive, platelet rich plasma (PRP) gel, platelet poor plasma (PPP) gel, Matrigel, Monostearoyl Glycerol co-Succinate (MGSA), Monostearoyl Glycerol co-Succinate/polyethylene glycol (MGSA/PEG) copolymers, laminin, elastin, proteoglycans, polyhydroxybutyrate (PHB), poly(vinyl pyrrolidone) (PVP), polylactide (PLA), polyglycolide (PGA), polycaprolactone (PCL), and their copolymers, non-woven VICRYL® (Ethicon, Inc., Somerville, N.J.), MONOCRYL material, fibrin, non-woven poly-L-lactide, and non-woven PANACRYL (Ethicon, Inc., Somerville, N.J.). Polymers may include aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, polypropylene fumarate), polyurethane, poly(ester urethane), poly(ether urethane), and blends and copolymers thereof. Suitable synthetic polymers for use in examples described herein may also include biosynthetic polymers based on sequences found in collagen, laminin, glycosaminoglycans, elastin, thrombin, fibronectin, starches, poly(amino acid), gelatin, alginate, pectin, fibrin, oxidized cellulose, chitin, chitosan, tropoelastin, hyaluronic acid, silk, ribonucleic acids, deoxyribonucleic acids, polypeptides, proteins, polysaccharides, polynucleotides, and combinations thereof. Other suitable materials or combinations of materials that may be used will be apparent to those of ordinary skill in the art in view of the teachings herein. It should also be understood that tissue mixed with a scaffold material may have any suitable particle size, and that the resulting mixture may at least initially have the consistency of a slurry or have any other suitable consistency. In some versions, the tissue particles include an effective amount of viable cells that can migrate out of the tissue particle and populate the scaffold. The term "viable," as used herein, should be understood to include a tissue sample having one or more viable cells.

In some versions, one or more components in a medical fluid or tissue treatment composition comprise one or more healing agents that promote tissue regeneration at a target site (e.g., within a fistula) and/or accelerate tissue healing at the target site. Healing agents may include any of a variety of biocompatible materials that accelerate tissue healing and/or promote tissue regeneration. Such biological components may include, for example, growth factors, proteins, peptides, antibodies, enzymes, platelets, glycoproteins, hormones, cytokines, glycosaminoglycans, nucleic acids, analgesics, viruses, isolated cells, or combinations thereof. The medical fluid may further include one or more additional treatment components that prevent infection, reduce inflammation, prevent or minimize adhesion formation, and/or suppress the immune system. In some versions where a scaffold is used in conjunction with a tissue treatment composition, one or more of these additional biological components or additional treatment components may be provided on and/or within the scaffold. Some examples described herein may also include one or more adhesive agents in conjunction with viable tissue fragments.

Examples described herein relate to the repair (e.g., closing) of lumens in a patient, such as anal fistulas and other types of fistulas. In particular, examples described herein include devices used in at least part of a process to create and/or deliver tissue repair compositions or medical fluid into a lumen such as an anal fistula. It should be understood that anal fistulas and/or other types of fistulas may be relatively difficult to repair (e.g., close) in some settings. The goal of a surgical repair of an anal fistula may be to close the fistula with as little impact as possible on the sphincter muscles. In some settings, a tissue repair composition or medical fluid as described herein may be delivered into the fistula as a liquid composition, a flowable gel or paste, a scaffold plug, or a combination of the two or more of the foregoing (e.g., a porous scaffold plug loaded with a medical fluid composition, etc). Anal fistulas may also be repaired by injecting bioresorbable fibrin glue into the fistula that seals the fistula and promotes tissue growth across the fistula in order to provide permanent closure. Various bioresorbable plugs may also be used to repair anal fistulas. The plug may comprise, for example, collagen protein, tissue, stem cells, and/or other medical fluid components referred to herein; and the plug may be inserted into the fistula where it promotes tissue growth across the fistula as the plug dissolves. If desired, the plug may be secured in place using one or more fasteners and/or one or more adhesive agents. As another merely illustrative example, a medical fluid may be introduced within the fistula, and the medical fluid may eventually harden and then dissolve and/or be absorbed.

Prior to applying a medical fluid to a fistula, it may be desirable in some settings to debride the wall of a fistula (e.g., to remove epithelial cells, etc.), otherwise agitate the wall of the fistula, and/or otherwise treat the walls of the fistula. While examples herein are discussed in the context of an anorectal fistula, it should be understood that the following exemplary devices and techniques may be readily applied to various other types of fistulae. Similarly, while the present example relates to treatment of a fistula in a patient, it should also be understood that the following exemplary devices and techniques may be readily applied with respect to various other types of conditions in a patient. Other suitable ways in which the devices and techniques described herein may be used will be apparent to those of ordinary skill in the art in view of the teachings herein.

As used herein, the term "fluid communication" (or in some contexts "communication") means that there is a path or route through which fluid (gas, liquid or other flowable material) may flow between two components, either directly or through one or more intermediate components. Similarly, the term "conduit" encompasses a conduit within or integrated with a valve. In other words, fluid communication between two components means that fluid can flow from one component to another but does not exclude an intermediate component (e.g., a valve, etc.) between the two recited components that are in fluid communication. Similarly, two or more components may be in mechanical "communication" with each other even if intermediate components are interposed between those two or more components.

II. Exemplary Tissue Harvesting and Processing Device Having Stationary Screen

FIG. 1 depicts an exemplary tissue harvesting and morcellating device (200). In this example, tissue harvesting and morcellating device (200) is a modified version of an otherwise conventional biopsy device, such as one of the biopsy devices taught in any of the U.S. Patents, U.S. Patent Application Publications, and U.S. Non-Provisional Patent Applications cited above. In particular, tissue harvesting and morcellating device (200) of this example comprises a body (210) and an elongate needle (220) extending distally from body (210). Body (210) is sized and configured to be held and operated by a single hand of a user, though body (210) may be configured to mount to a table, fixture, or other structure in addition to or in lieu of being configured to be held and operated by hand. Needle (220) includes a closed, tissue piercing distal tip (222) and a side aperture (224) located proximal to tissue piercing distal tip (220). A hollow tubular cutter (230) is configured to reciprocate and rotate within needle (220). In particular, cutter (230) may be retracted to a proximal position, in which the distal cutting edge (232) of cutter (230) is located proximal to the proximal edge of side aperture (224), to allow tissue to protrude in side aperture (224). Cutter (230) may then be extended to a distal position, in which distal cutting edge (232) of cutter (230) is located distal to the distal edge of side aperture (224), to sever tissue protruding in side aperture. The severed tissue specimen or core may then be communicated proximally through cutter (230) into body (210).

Body (210) of the present example includes a morcellating apparatus (240), a cutter actuation mechanism (250), and a vacuum source (260). Vacuum source (260) is in fluid communication with the hollow interior of cutter (230) via morcellating apparatus (240) in this example. Vacuum source (260) is operable to draw a vacuum through the hollow interior of cutter (230). Such a vacuum may assist in drawing tissue into side aperture (224) when cutter (230) is retracted. In addition, such a vacuum may assist in transporting a severed tissue specimen or core proximally through cutter (230) into morcellating apparatus (240). Needle (220) may also include a separate opening and/or lumen (e.g., a lumen that is parallel to and offset from a lumen in which cutter (230) is positioned, etc.) that provides venting and/or pressurized air to provide a pressure differential facilitating proximal transport of severed tissue through cutter (230). While vacuum source (260) is shown as being part of body (210) in the present example, it should be understood that an external vacuum source (260) may be used in addition to or in lieu of internal vacuum source (260). For instance, a tube or other type of conduit may couple body (210) with an external vacuum source.

Cutter actuation mechanism (250) of the present example is operable to translate and rotate cutter (230). Cutter actuation mechanism (250) may be configured in accordance with the teachings of any of the patents or patent publications cited herein, or in any other suitable fashion. While cutter actuation mechanism (250) is shown as being part of body (210) in the present example, it should be understood that one or more components of cutter actuation mechanism (250) may instead be provided external to body (210). By way of example only, an external device may communicate rotary power to body (210) via speedometer cables or in some other fashion, and cutter actuation mechanism (250) in body (210) may include components operable to convert such rotary power to linear motion and/or rotary motion of cutter (230). Various suitable ways in which cutter actuation mechanism (250) may be configured will be apparent to those of ordinary skill in the art in view of the teachings herein. It should also be understood that some versions of tissue harvesting and morcellating device (200) may lack cutter (230) and/or cutter actuation mechanism (250) altogether. For instance, in some other versions, needle (220) is a conventional coring needle having an open distal end.

Morcellating apparatus (240) of the present example comprises a morcellating feature (242) and a morcellated tissue chamber (244). Morcellating feature (242) is operable to morcellate tissue cores that are communicated proximally through cutter (230) and needle (220). Morcellated tissue chamber (244) is configured to hold the resulting morcellated tissue. In some versions, morcellating feature (242) is added to what would otherwise be a conventional tissue sample holder in an otherwise conventional biopsy device. Examples of various forms that morcellating apparatus (240) may take will be described in greater detail below. It should therefore be understood that the various examples of morcellating devices described below may be readily incorporated into various forms of tissue harvesting and morcellating device (200). It should also be understood that the various examples of morcellating devices described below may alternatively be kept separate from a tissue harvesting device. For instance, a tissue harvesting device (e.g., coring needle having open distal end, conventional biopsy device with side aperture in needle, etc.) may be used to perform initial harvesting of tissue from the patient. The harvested tissue may then be removed from the tissue harvesting device and then be deposited into any of the various examples of morcellating devices described below for morcellation. Other suitable devices and systems in which the morcellating devices described below may be incorporated will be apparent to those of ordinary skill in the art in view of the teachings herein. Similarly, other suitable ways in which tissue may be harvested and morcellated, as well as various suitable relationships between tissue harvesting devices and tissue morcellating devices, will be apparent to those of ordinary skill in the art in view of the teachings herein. It should also be understood that morcellated tissue may be mixed with any of the various medical fluid components referred to herein (among others), such as to form a tissue treatment composition.

Figure 2:
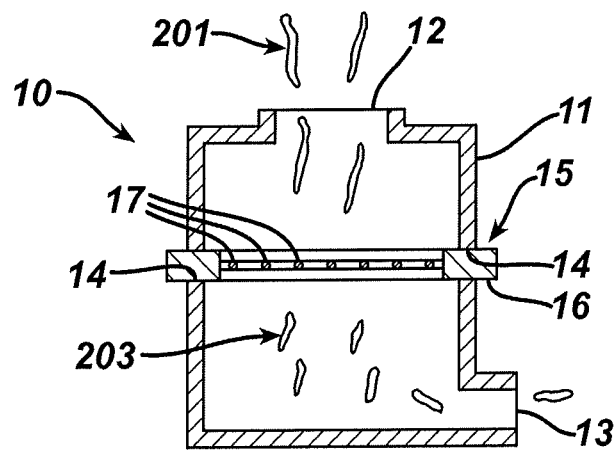
FIG. 2 depicts a side cross-sectional view of an exemplary tissue morcellating device.
Figure 3:
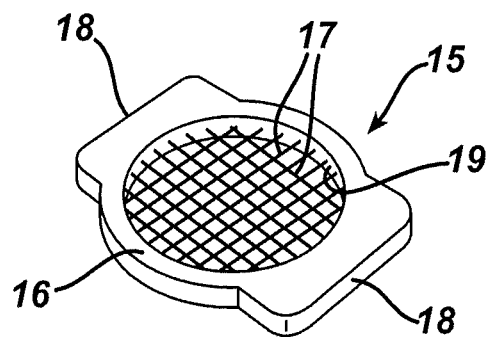
FIG. 3 depicts a perspective view of a screen member of the morcellating device of FIG. 2.

FIGS. 2-3 depict an exemplary morcellating apparatus (10) that may be used to morcellate tissue specimens (201) collected from a patient. Morcellating apparatus (10) is depicted as a stand-alone device that may be used separately from the harvesting device that is used to collect soft tissue specimens (201) from a patient. Other examples of morcellating apparatus shown and described herein are also configured as stand-alone devices, separate from any tissue harvesting device. However, it should be understood that morcellating apparatus (10) as well as the other examples herein may be incorporated into, or operatively connected to, various types of tissue harvesting devices in order to morcellate soft tissue specimens (201) as they are collected from a patient and/or shortly after they are collected from the patient. By way of example only, morcellating apparatus (10) as well as the other examples herein may be incorporated into tissue harvesting and morcellating device (200) described above. For instance, morcellating apparatus (10) as well as the other examples herein may serve as morcellating apparatus (240) in tissue harvesting and morcellating device (200) described above. Other suitable types of devices in which morcellating apparatus (10) as well as the other examples herein may be incorporated will be apparent to those of ordinary skill in the art in view of the teachings herein.

Morcellating apparatus (10) of the present example includes a housing (11), which defines a morcellating chamber therein. A tissue inlet (12) is provided at one end of housing (11) and a tissue outlet (13) is provided at another end of housing (11). In this manner, the morcellating chamber extends axially between inlet (12) and outlet (13). As further described herein, tissue specimens (201) may be supplied to, or inserted into, housing (11) through tissue inlet (12), and the morcellated tissue specimens may be expelled or removed from housing (11) through outlet (13). While housing (11), particularly the morcellating chamber defined therein, is depicted as having a generally cylindrical configuration, any of variety of alternative configurations may be employed.

A screen member (15) is mounted within housing (11) and comprises a frame portion (16) having a central opening (19) formed therein. While central opening (19) is depicted as having a circular shape, other configurations may be readily employed. Frame portion (16) of this example also has a generally circular configuration, and includes a pair of mounting tabs (18) that extend from opposite sides thereof. The outer diameter of frame portion (16) may be sized to match the inner diameter of housing (11), and mounting tabs (18) may be sized and configured to facilitate the securement of screen member (15) in housing (11). For example, housing (11) of the present example has a pair of slots (14) located on opposite sides of housing (11). Screen member (15) is positioned in housing (11) such that tab members (18) extend through slots (14), as shown, with frame portion (16) spanning the inner diameter of housing (11). Of course any of a variety of other structures and techniques may be used to provide a cutting screen extending transversely across the morcellating chamber, such as by gluing a screen member inside the morcellating chamber, etc.

Screen member (15) also includes a plurality of elongate cutting members (17) that extend transversely across central opening (19) of frame portion (16), and are arranged so as to define a plurality of passageways therebetween. In the present example, elongate cutting members (17) comprise wire members which are arranged in a grid pattern. In this manner, rectangular passageways are provided between adjacent wires. Of course the rectangular grid pattern is merely exemplary, as wire cutting members may be arranged in any of a variety of other patterns. Furthermore, elongate cutting members (17) may alternatively be formed of blades or flat strips of metal instead of being formed by wires. Other suitable ways in which cutting members (17) may be formed, configured, and arranged will be apparent to those of ordinary skill in the art in view of the teachings herein. Similarly, various suitable materials and combinations of materials that may be used to form cutting members (17) will be apparent to those of ordinary skill in the art in view of the teachings herein.

During use, soft tissue specimens (201) collected from a patient enter housing (11) through tissue inlet (12). The tissue specimens may be manually placed into housing (11), between screen member (15) and inlet (12) (e.g., above screen member (15) when the apparatus is oriented as shown in FIG. 2). Alternatively, morcellating apparatus (10) may be placed in communication with a source of soft tissue specimens (201), such as by attaching morcellating apparatus (10) to a conduit supplying tissue specimens (201) at inlet (12). By way of example only, the collection chamber of a biopsy device may be attached at inlet (12) such that soft tissue specimens (201) are delivered to the interior of housing (11). In some other versions, tissue specimens (201) are fed into inlet (12) by injecting tissue specimens (201) from a coring needle. Other suitable ways in which tissue specimens (201) may be communicated into inlet (12) will be apparent to those of ordinary skill in the art in view of the teachings herein.

In order to morcellate soft tissue specimens (201) into smaller minced pieces (203), tissue specimens (201) are urged through screen member 15. As tissue specimens (201) are urged through screen member (15), wire cutting members (17) will cut the soft tissue into smaller pieces (203), which pass through screen member (15), as shown. Soft tissue specimens (201) may be urged through screen member (15) in a variety of ways. For example, tissue specimens (201) may be pulled through screen member (15) by a vacuum being provided at outlet (13), with inlet (12) being vented to provide a pressure differential. A fine screen or other type of filter may be provided at outlet (13) or elsewhere to prevent morcellated tissue from reaching the vacuum source. In addition or in the alternative, a pressurized medium (e.g., pressurized air, saline, etc.) may be communicated through inlet (12) to drive tissue specimens (201) through screen member (15). Again, a fine screen or other type of filter may be provided at outlet (13) or elsewhere to allow the pressurized medium to pass through outlet (13) without letting the morcellated tissue pass through outlet (13). Various other suitable ways in which tissue specimens (201) may be urged through screen member (15) to morcellate such tissue specimens (201) will be apparent to those of ordinary skill in the art in view of the teachings herein.

Figure 4:
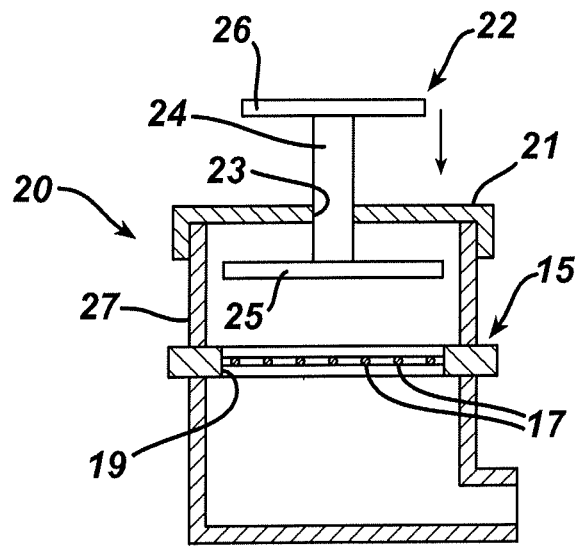
FIG. 4 depicts a side cross-sectional view of an exemplary variation of the tissue morcellating device of FIG. 2, including a press assembly.

In an exemplary alternative version, soft tissue specimens may be forced through screen member (15) using a mechanical press assembly. FIG. 4 depicts an example of such an alternative morcellating apparatus (20), which is similar in construction to morcellating apparatus (10). In the example shown in FIG. 4, once tissue specimens are placed into housing (27) above screen member (15), a cap (21) may be secured over one end of housing (27). Cap (21) includes a press assembly (22) moveably mounted thereto. Press assembly (22) includes a press plate (25), an actuating rod (24) attached to press plate (25) at one end of actuating rod (24), and a handle (26) attached to the other end of actuating rod (24). Actuating rod (24) is also positioned so as to extend through an opening (23) in cap (21). Plate (25) may have a shape and size similar to central opening (19) in screen member (15). In addition, press assembly (22) and opening (23) in cap (21) are configured so that when cap (21) is placed over the inlet opening of housing (27), press plate (25) will be substantially aligned with central opening (19) of screen member (15). Handle (26) may then be urged in the direction shown, thereby urging press plate (25) towards wire cutting members (17) of screen member (15). The soft tissue specimens will be urged through screen member (15) as press plate (25) is forced toward wire cutting members (17) of screen member (15). This results in the soft tissue specimens being cut into smaller minced pieces as the tissue specimens are urged through screen member (15). It should be understood that press plate (25) may also be used in versions where fluid is provided within the interior of morcellating apparatus (20). For instance, press plate (25) may act as a piston that is operable to force both tissue and fluid through screen member (15). It is also contemplated that more than one of the various mechanisms for urging tissue specimens through a cutting screen may be employed. For example, a mechanical press may be used in conjunction with a pressurized medium and/or a vacuum that pulls tissue specimens through the cutting screen.

Figure 5:
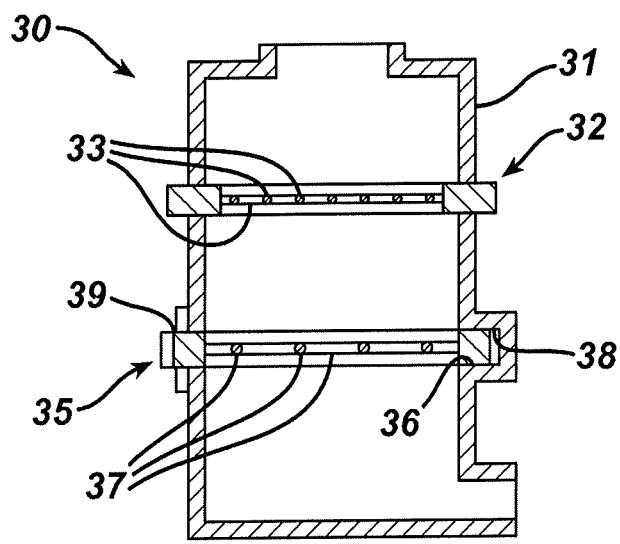
FIG. 5 depicts a side cross-sectional view of another exemplary tissue morcellating device.
Figure 6:
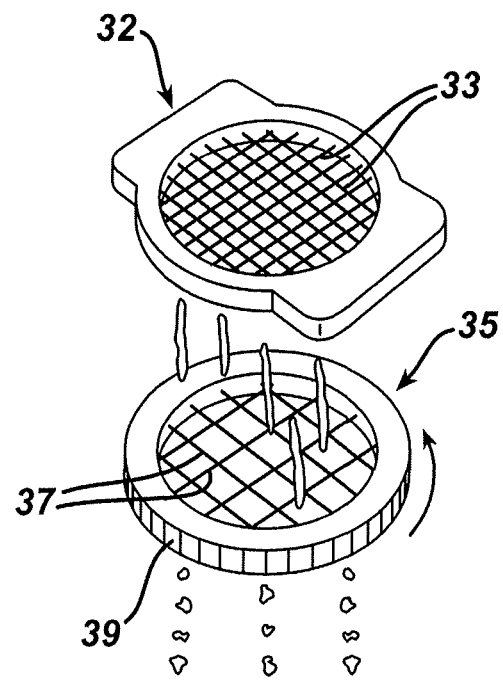
FIG. 6 depicts a perspective view of a pair of screen members of the morcellating device of FIG. 5.

III. Exemplary Tissue Harvesting and Processing Device Having Stationary Screen and Rotating Screen FIGS. 5-6 depict yet another exemplary morcellating apparatus (30). In this example, a first screen member (32) remains stationary during use, while a second screen member (35) is rotated within housing (31) during use. First screen member (32) may be configured similar to screen member (15) of the example shown in FIGS. 2-3, and may also be mounted within housing (31) in a similar manner. Also, tissue specimens may be urged through screen member (32) in one or more of the various ways in which tissue specimens may be urged through screen member (15) as described above, such that tissue specimens are cut by wire cutting members (33) of first screen member (32). Wire cutting members (33) may be arranged, for example, in a grid pattern similar to that for screen member (15). Of course, any other suitable configuration and/or arrangement may be used.

Second screen member (35) of the present example generally comprises a circular frame having a central opening (36) therethrough. In the present example, central opening (36) is sized and shaped to approximate the inner diameter of housing (31). It should be understood, though, that any other suitable size and/or shape may be used. Second screen member (35) also includes a plurality of elongate cutting members (37), which extend across central opening (36) of the frame. Elongate cutting members (37) are arranged so as to define a plurality of passageways therebetween. In the present example, elongate cutting members (37) comprise wire members that are arranged in a grid pattern. In some other versions, elongate cutting members (37) are angularly arranged about a central region of central opening (36), such that elongate cutting members (37) radiate outwardly from the central region of central opening (36), providing gaps shaped like pie wedges. Of course, any other suitable configuration may be used. As shown in FIG. 6, wire cutting members (37) of second screen member (35) are arranged in the present example so as to be spaced from one another a greater distance than the wire cutting members (33) of first screen member (32), providing a coarser mesh. Alternatively, wire cutting members (37) may be arranged so as to have the same, or even smaller spacing (e.g., finer mesh) than wire cutting members (33).

Second screen member (35) in FIG. 5 is rotatably mounted within housing (31). In particular, a channel (38) extends about at least a portion of the interior circumference of housing (31), with second screen member (35) being received in channel (38). In the present example, channel (38) does not extend around the entire circumference, such that a portion of the exterior circumference (39) of second screen member (35) extends outwardly from housing (31). In this fashion, a portion of second screen member (35) will be exposed outside housing (31) such that second screen member (35) may be rotated during use. By way of example only, outer circumference (39) of second screen member (35) may be knurled and/or have any other suitable features or properties to facilitate hand rotation of second screen member (35) within housing (31). Alternatively, outer circumference (39) may comprise gear teeth that may be used to drivingly rotate second screen member (35) using a driven, and suitably-shaped, drive gear. The drive gear may be driven manually (as further described herein) or by a motor or other drive device (e.g., a motor provided in a tissue harvesting device in which morcellating apparatus (30) is incorporated, etc.).

Morcellating apparatus (30) may be used in a manner similar to morcellating apparatus (10) of FIGS. 2-3. For instance, in an exemplary use, soft tissue specimens are positioned within housing (31), between first screen member (32) and the inlet end of housing (31). The tissue specimens are then urged through first screen member (32) and, thereafter, through second screen member (35), while second screen member (35) is rotated. The soft tissue specimens are cut into smaller pieces by first screen member (32), and are then cut into even smaller pieces by the rotating second screen member (35). In particular, tissue specimens may be first extruded through first screen member (35), such that first screen member (32) cuts tissue specimens into smaller pieces in a vertical direction as the tissue specimens are extruded through first screen member (32). During this extrusion, rotating second screen member (35) cuts the extruded pieces in a horizontal direction to cut the tissue specimens into even smaller pieces.

In some versions, first screen member (32) is configured such that tissue will not be extruded or otherwise communicated through a central region of first screen member (32) (e.g., above a region where second screen member (35) is not significantly rotating, etc.). In other words, it should be understood that the mesh of first screen member (32) may have a configuration that is non-uniform (e.g., tighter weave in the central region of first screen member (32), etc.).

It should be understood that, because second screen member (35) is rotating as the tissue specimens are urged therethrough, the tissue specimens will be cut into even smaller pieces. In particular, rotating second screen member (35) relative to first screen member (32) may provide a shearing action by cutting members (33, 37) as tissue passes through first and second screen members (32, 35). While FIG. 5 shows first and second screen members (32, 35) being substantially separated from each other, it should be understood that first and second screen members (32, 35) may instead be positioned substantially closer to each other to facilitate mincing of tissue through shearing action by cutting members (33, 37). In some versions, the separation between first and second screen members (32, 35) may be adjusted to selectively vary the size of minced tissue particles that result from tissue specimens passing through screen members (32, 35). Various suitable ways in which morcellating apparatus (30) may be constructed to provide such adjustability will be apparent to those of ordinary skill in the art in view of the teachings herein.

Although second screen member (35) is depicted in FIG. 6 as being rotated counter-clockwise, second screen member (35) may be rotated in either direction—or even clockwise and counter-clockwise, in alternating fashion (i.e., reciprocally rotated, in back and forth fashion). It should also be understood that tissue specimens may be urged through screen members (32, 35) of morcellating apparatus (30) in one or more of the ways described previously with respect to the apparatus of FIGS. 2-3 or in any other suitable way. While FIGS. 5-6 depict morcellating apparatus (30) having one stationary screen member (32) and one rotating screen member (35), it should be understood that any number of stationary and/or rotating screen members may be employed. By way of example only, one or more additional rotating screens may be positioned downstream of second screen (35) in FIG. 5. Such additional screens may have the same mesh size, or a different mesh size, as second screen (35).

Figure 7:
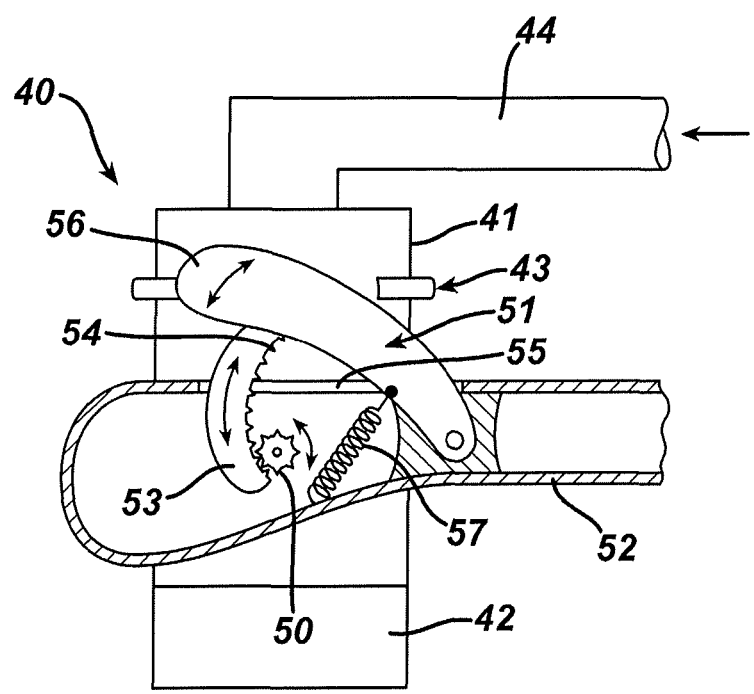
FIG. 7 depicts a side view of another exemplary tissue morcellating device, with components of an actuation mechanism shown in cross-section.
Figure 8:
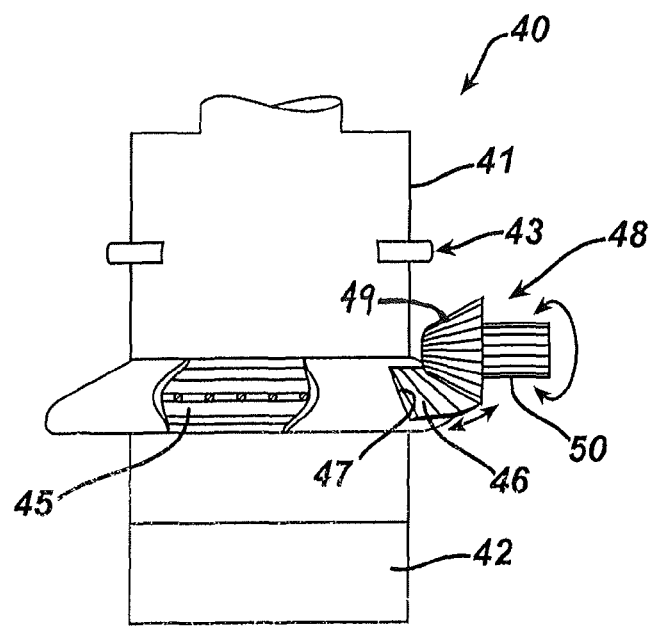
FIG. 8 depicts another side view of the morcellating device of FIG. 7, with other components shown in cross-section.

While the example shown in FIGS. 5-6 is depicted as providing for manual rotation of second screen member (35), it should be understood that various mechanical arrangements may be used to facilitate rotation of one or more screen members (32, 35). One merely illustrative example of such a morcellating apparatus (40) is shown in FIGS. 7-8, in which a movable handle (51) is used to rotate a second screen member (45). Morcellating apparatus (40) is similar to that shown in FIGS. 5-6, and includes a first stationary screen member (43) and a second rotating screen member (45), both of which are mounted in a housing (41) similarly to that described above with respect to FIGS. 5-6. In the present example, however, a collection chamber (42) is provided at an end of housing (41) in place of an opening through which morcellated tissue particles are removed or expelled. Collection chamber (42) may be attached to the end of housing (41) in a variety of ways, such as by a bayonet mount or by mating threads on collection chamber (42) and housing (41), etc. In this manner, after tissue specimens have been morcellated, collection chamber (42) is simply removed (e.g., unscrewed) from housing (41) in order to retrieve the morcellated tissue. It should also be noted that the end surface of collection chamber (42) may be foraminous in order to allow, for example, fluid to be expelled from morcellating apparatus (40) during use. This may be useful, for example, when tissue specimens are supplied to morcellating apparatus (40) by being entrained in a pressurized medium. In this manner, the entraining medium (e.g., air or another fluid such as saline) will be expelled through the end surface of collection chamber (42). Alternatively, one or more other portions of housing (41) downstream of second screen member (45) may be foraminous in nature in order to allow entraining medium to be expelled during use.

As also seen in FIG. 7, a specimen conduit (44) may be provided in order to supply tissue specimens to morcellating apparatus (40). The interior of specimen conduit (44) is in fluid communication with the interior of housing (41). Specimen conduit (44) may also be in fluid communication with a source of tissue specimens, such as a tissue harvesting device (200) as described above. Tissue specimens may be delivered to the interior of housing (41), upstream of first screen member (45), for example, by entrainment in a medium flowing through specimen conduit (44). It should be understood that tissue may be communicated to and/or through morcellating apparatus (40) in any of the various manners described above with respect to any other morcellating apparatus (10, 20, 30) or in any other suitable manner.

First screen member (43) in morcellating apparatus (40) of the present example is configured similarly to stationary screen members (15, 32) described above. Second screen member (45) in morcellating apparatus (40) is rotatably mounted in housing (41), as shown in FIG. 8, in a manner similar to that described above with respect to FIG. 5. As before, second screen member (45) may have a wire cutting member grid pattern having a coarser mesh size than first screen member (43) (or finer, or the same, etc.). In the present example, however, the outer circumference of second screen member (45) comprises a bevel gear (46), part of which extends outwardly of housing (41) through a partially circumferential opening (47) in housing (41). In some versions, bevel gear (46) extends about the full circumference of second screen member (45). In some other versions, bevel gear (46) extends only about part of the circumference of second screen member (45).

In the present example, a drive gear (48) is provided in order to rotate second screen member (45). Drive gear (48) includes a first bevel gear portion (49) configured to drivingly mate with bevel gear (46) of second screen member (45). In this manner, rotation of first bevel gear portion (49) of drive gear (48) will rotate second screen member (45). A second gear portion (50) is also provided on drive gear (48), with its axis of rotation corresponding to that of first bevel gear portion (49). As shown in FIG. 7, second gear portion (50) is rotated by a rocking handle (51), which is pivotally attached to a fixed grip (52) and extends outwardly from grip (52) through slot (55) in grip (52). Handle (51) may be resiliently biased outwardly away from grip (52) by a spring (57), as shown. A rack member (53) having a plurality of gear teeth (54) along one edge extends away from handle (51) into grip (52). Rack member (53) may be curved, as shown; or may have any other suitable configuration. Rack member (53) is configured for driving engagement with second gear portion (50) of drive gear (48). In this manner, as end portion (56) of handle (51) is urged toward grip (52), rack member (53) will cause second gear portion (50) to rotate as shown. This rotation provides concomitant rotation of second screen member (45), through first bevel gear portion (49). If handle (51) is resiliently biased, as shown, the second screen member (45) will rotate in the opposite direction when handle (51) is releasably allowed to return to the starting position shown in FIG. 7.

During an exemplary use of morcellating apparatus (40), as tissue specimens are urged through the first and second screen members (43, 45) (e.g., via entrainment in a pressurized fluid, etc.), the user may simply squeeze end portion (56) of handle (51) toward fixed grip (52) in order to cause rotation of second screen member (45). By repeatedly squeezing and releasing, second screen member (45) will repeatedly and reciprocally rotate in order to further cut the tissue specimens, such as through a shearing action provided by cooperation between first and second screen members (43, 45). Alternatively, first bevel gear portion (49) could simply be directly driven by a motor (not shown). Similarly, second gear portion (50) may be driven by any of a variety of means, such as one or more additional gears meshing therewith, with one of the additional gears being driven by a motor or other mechanism. Once the desired amount of tissue has been morcellated or minced, collection chamber (42) may be removed from housing (41) and the morcellated or minced tissue in collection chamber (42) may be processed and used in accordance with the teachings of any of the patents or patent publications cited herein, may be mixed with any of the various medical fluid components referred to herein (among others) to form a tissue treatment composition, and/or may be processed and used in any other suitable fashion.

Figure 9:
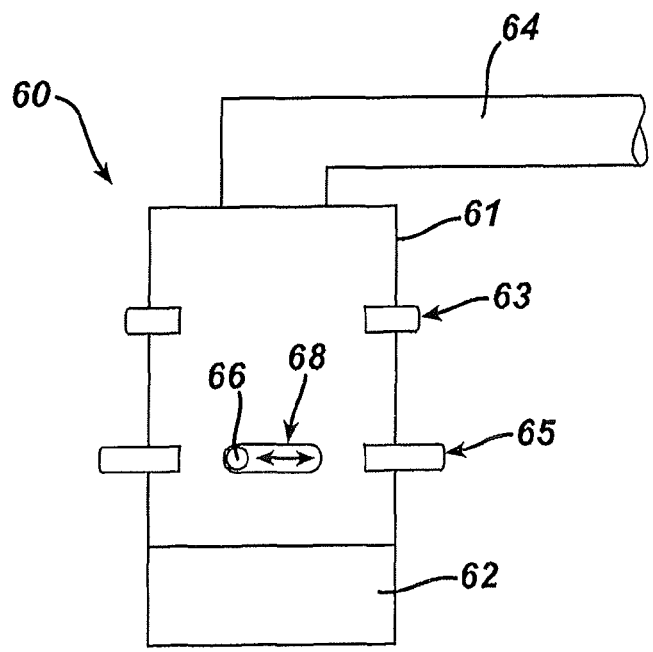
FIG. 9 depicts a side view of another exemplary tissue morcellating device, with components of an actuation mechanism omitted.
Figure 10:
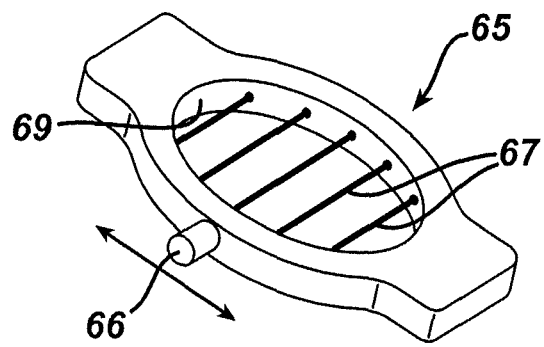
FIG. 10 depicts a perspective view of a screen member of the morcellating device of FIG. 9.
Figure 11:
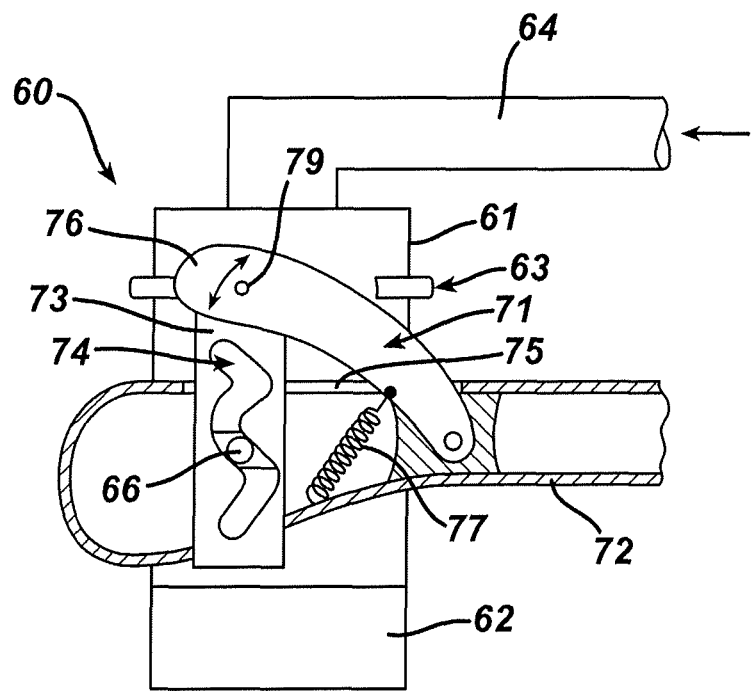
FIG. 11 depicts a side view of the morcellating device of FIG. 9, with components of an actuation mechanism shown in cross-section.

IV. Exemplary Tissue Harvesting and Processing Device Having Reciprocating Screen FIGS. 9-11 depict yet another exemplary morcellating apparatus (60). This morcellating apparatus (60) is similar to morcellating apparatus (40) in several respects as described in greater detail below. However, the rotating second screen member (35) has been replaced by a reciprocating screen member (65) in morcellating apparatus (60). For instance, like morcellating apparatus (40), morcellating apparatus (60) includes a specimen conduit (64) for communicating tissue specimens into the interior of housing (61). Tissue specimens may thus be delivered to the interior of housing (61) via specimen conduit (64) in accordance with the above teachings relating to delivery of tissue specimens to the interior of housing (41) via specimen conduit (44); or in any other suitable fashion. In addition, morcellating apparatus (60) includes a stationary screen member (63), which remains stationary during use. Tissue specimens may be urged through screen member (63) in one or more of the various ways in which tissue specimens may be urged through screen member (15) as described above, such that tissue specimens are cut by wire cutting members (not shown) of stationary screen member (63). Such wire cutting members may be arranged, for example, in a grid pattern similar to that for screen member (15). Of course, any other suitable configuration and/or arrangement may be used.

Morcellating apparatus (60) of the present example also includes a collection chamber (62) provided at an end of housing (61). Collection chamber (62) may be attached to the end of housing (61) in a variety of ways, such as by a bayonet mount or by mating threads on collection chamber (62) and housing (61), etc. In this manner, after tissue specimens have been morcellated, collection chamber (62) is simply removed (e.g., unscrewed) from housing (61) in order to retrieve the morcellated tissue. It should also be noted that the end surface of collection chamber (62) may be foraminous in order to allow, for example, fluid to be expelled from morcellating apparatus (60) during use. This may be useful, for example, when tissue specimens are supplied to morcellating apparatus (60) by being entrained in a pressurized medium. In this manner, the entraining medium (e.g., air or another fluid such as saline) will be expelled through the end surface of collection chamber (62). Alternatively, one or more other portions of housing (61) downstream of second screen member (65) may be foraminous in nature in order to allow entraining medium to be expelled during use.

Reciprocating screen member (65) may be configured similarly to screen member (15) shown in FIG. 3. However, instead of wire cutting members being arranged in a grid pattern, reciprocating screen member (65) has a plurality of wire members (67) that extend across central opening (69) parallel to one another in this example. Thus, elongate passageways are provided between adjacent wire members (67). During use, reciprocating screen member (65), located downstream of stationary first screen member (63), is reciprocated back and forth as shown, in order to cut the tissue specimens into smaller pieces. For instance, cooperation between wire members (67) of reciprocating screen member (65) and wire members (not shown) of stationary first screen member (63) may cut the tissue specimens into smaller pieces through a shearing action. It should be understood that stationary first screen member (63) and reciprocating screen member (65) may be positioned closer to each other than is shown in FIG. 9; and that the spacing of stationary first screen member (63) and reciprocating screen member (65) (as well as the spacing and/or configuration of wire members (67), etc.) may affect the size of the pieces that are cut by screen member (63) and reciprocating screen member (65). Various other suitable configurations of, features of, and relationships between first screen member (63) and reciprocating screen member (65) will be apparent to those of ordinary skill in the art in view of the teachings herein.

In the present example, a pin (66) extends outwardly and unitarily from reciprocating screen member (65), such that pin (66) is movable to reciprocate screen member (65) back and forth. As shown in FIG. 9, pin (66) extends through a transverse slot (68) formed in housing (61). Slot (68) provides sufficient clearance to allow pin (66) to reciprocate during reciprocation of screen member (65). As shown in FIG. 11, a cam member (73) is operable to drive pin (66) to reciprocate screen member (65). It should be understood that cam member (73) and other actuation components described below are omitted from FIG. 9 to better show the relationship between slot (68) and pin (66).

As shown in FIG. 11, cam member (73) is vertically movable by a rocking handle (71), which is pivotally attached to a fixed grip (72) and extends outwardly from grip (72) through slot (75) in grip (72). Handle (71) may be resiliently biased outwardly away from grip (72) by a spring (77), as shown. Cam member (73) extends away from handle (71) into grip (72). Cam member (73) is substantially straight in the present example, though it should be understood that cam member (73) may alternatively have any other suitable configuration. In addition, cam member (73) is pivotally secured to handle (71) by a pivot pin (79), which allows cam member (73) to maintain a substantially consistent orientation (e.g., vertical orientation) as handle (71) is pivoted relative to grip (72). In particular, when handle (71) is squeezed downwardly toward grip (72), cam member (73) is driven downwardly while maintaining a substantially consistent orientation. Cam member (73) is operable to drive reciprocating screen member (65) back and forth as cam member (73) is moved linearly. In particular, cam member (73) defines a zigzag shaped slot (74). Pin (66) is disposed through slot (74). In this manner, as end portion (76) of handle (71) is urged toward grip (72), the engagement between pin (66) and slot (74) of cam member (73) will cause pin (66) and screen member (65) to move back and forth. If handle (71) is resiliently biased, as shown, the second screen member (65) will again move back and forth when handle (71) is releasably allowed to return to the starting position shown in FIG. 11. It should be understood that grip (72) and/or housing (61) may include guide features (not shown) configured to substantially maintain the orientation (e.g., vertical orientation) of cam member (73) as cam member (73) is moved by handle (71). It should also be understood that cam member (73) may be driven by one or more solenoids, one or more motors, one or more hydraulic or pneumatic actuators, and/or by a variety of other components or devices in addition to or in lieu of being driven by handle (71). Similarly, pin (66) may be driven by one or more solenoids, one or more motors, one or more hydraulic or pneumatic actuators, and/or by a variety of other components or devices in addition to or in lieu of being driven by cam member (73).

During an exemplary use of morcellating apparatus (60), as tissue specimens are urged through the first and second screen members (63, 65) (e.g., via entrainment in a pressurized fluid, etc.), the user may simply squeeze end portion (76) of handle (71) toward fixed grip (72) in order to cause reciprocation of second screen member (65). By repeatedly squeezing and releasing, second screen member (65) will repeatedly reciprocate in order to further cut the tissue specimens, such as through a shearing action provided by cooperation between first and second screen members (63, 65). Once the desired amount of tissue has been morcellated or minced, collection chamber (62) may be removed from housing (61) and the morcellated or minced tissue in collection chamber (62) may be processed and used in accordance with the teachings of any of the patents or patent publications cited herein, may be mixed with any of the various medical fluid components referred to herein (among others) to form a tissue treatment composition, and/or may be processed and used in any other suitable fashion.

Figure 12:
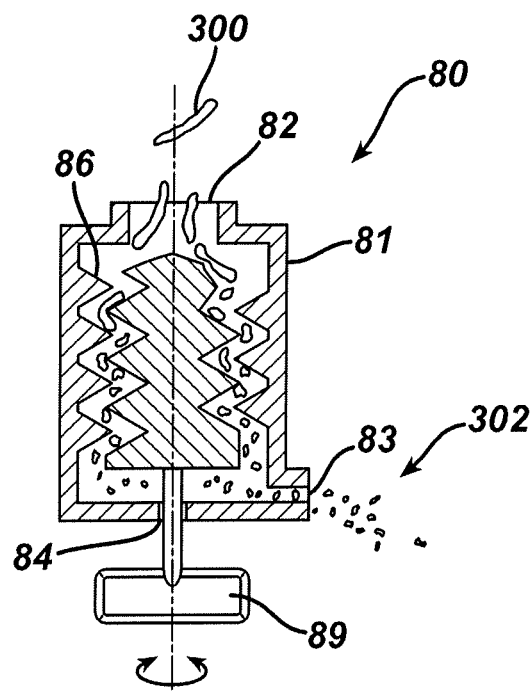
FIG. 12 depicts a side cross-sectional view of another exemplary tissue morcellating device.
Figure 13:
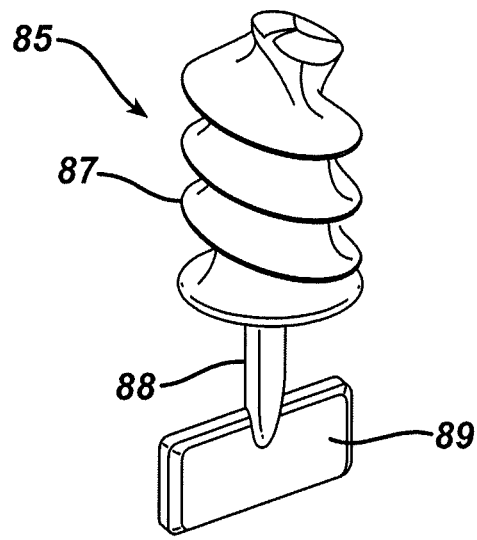
FIG. 13 depicts a perspective view of a cutting member of the morcellating device of FIG. 12.

V. Exemplary Tissue Harvesting and Processing Devices Having Elongate Cutting Member FIGS. 12-13 depict yet another exemplary morcellating apparatus (80), which comprises a housing (81) defining a tubular morcellating chamber therein, and a cutting member (85) rotatably positioned within the morcellating chamber. As best seen in FIG. 13, cutting member (85) is helically threaded such that a sharp cutting edge (87) extends around the periphery of cutting member (85). In some versions, cutting edge (87) is serrated. In the example shown, a shaft (88) extends away from an end of cutting member (85), and a handle (89) is provided at the other end of shaft (88) in order to facilitate manual rotation of cutting member (85). As shown in FIG. 12, cutting member (85) is disposed within housing (81). Housing (81) includes a central aperture (84) through which shaft (88) extends, such that the longitudinal axis of shaft (88) is aligned with the longitudinal axis of the morcellating chamber of housing (81). In some versions, a seal or gasket (not shown) is positioned within central aperture (84) about shaft (88), substantially preventing leakage of tissue and/or liquids along shaft (88). Such a seal or gasket may be configured to permit cutting member (85) (including shaft (88), etc.) to be rotated relative to housing (81).

Housing (81) includes a tissue inlet (82) formed at one end and a tissue outlet (83) formed at another end. Housing (81) further includes inwardly extending teeth (86) in its interior. Teeth (86) are positioned along at least part of the length of the morcellating chamber in housing (81), and may be provided in any suitable number/arrangement. In some other versions, teeth (86) are replaced with a helical internal threading, which may be substantially continuous, broken, or have various other configurations. Other suitable variations of teeth (86)

will be apparent to those of ordinary skill in the art in view of the teachings herein. As shown in FIG. 12, internal teeth (86) of housing (81) in the present example are configured to complement the threaded configuration of cutting member (85). In particular, cutting member (85) and internal teeth (86) are configured to cooperate to cut tissue specimens (300) into morcellated or minced tissue pieces (302) when cutting member (85) is rotated relative to housing (81). It should also be understood that cutting member (85) has a relatively loose fit within housing (81), allowing for some degree of vertical movement of cutting member (85) within housing (81) along the longitudinal axis of cutting member (85). Thus, cutting member (85) and housing (81) are sized and configured such that tissue may pass between cutting member (85) and internal teeth (86) to reach outlet (83); yet still be morcellated or minced by cutting member (85) and internal teeth (86) along the way. In some versions, teeth (86) and cutting member (85) are configured such that cutting member (85) moves longitudinally relative to housing (81) when cutting member (81) is rotated to morcellate or mince tissue specimens (300). In some other versions, teeth (86) and cutting member (85) are configured such that cutting member (85) does not move longitudinally relative to housing (81) when cutting member (81) is rotated to morcellate or mince tissue specimens (300). Various examples of such configurations will be apparent to those of ordinary skill in the art in view of the teachings herein.

Tissue specimens (300) may be introduced into housing (81) through inlet (82), and the morcellated tissue pieces (302) may be removed or expelled from housing (81) through outlet (83). Tissue specimens (300) may be manually placed into housing (81), or supplied via an entrainment medium (e.g., air, saline, or other fluid, etc.) under pressure such that the morcellated tissue pieces (302) are expelled from morcellating apparatus (80) through outlet (83). In addition or in the alternative, the threaded configuration of cutting member (85) and/or internal teeth (86) may assist in conveying tissue toward outlet (83) when cutting member (85) is rotated. The resulting morcellated or minced tissue (302) may then be processed and used in a medical fluid mixture as described herein and/or accordance with the above teachings of any of the patents or patent publications cited herein; or in any other suitable fashion.

It should be understood that cutting member (85) may be either rotated in just one direction or rotated in both directions (e.g., in a rocking action) in order to morcellate or mince tissue specimens (300). It should also be understood that, while handle (89) is rotated manually by a user to rotate cutting member (85) in the present example, cutting member (85) may alternatively be rotated by a motor or other device. Furthermore, morcellating apparatus (80) may be either provided as a stand-alone device or as a component of a tissue harvesting device. For instance, as with other morcellating apparatuses (10, 20, 30, 40, 60) described herein, morcellating apparatus (80) may be provided as morcellating apparatus (240) of tissue harvesting and morcellating device (200) described above. Other suitable features, configurations, uses, and contexts for morcellating apparatus (80) will be apparent to those of ordinary skill in the art in view of the teachings herein.

Figure 16:
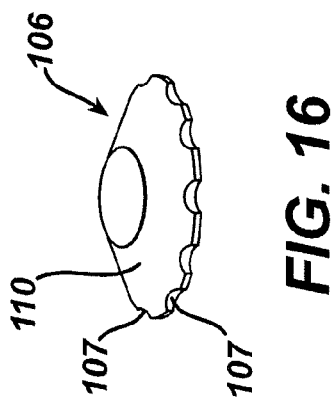
FIG. 16 depicts a perspective view of a cutting disc of the cutting member of FIG. 15.
Figure 15:
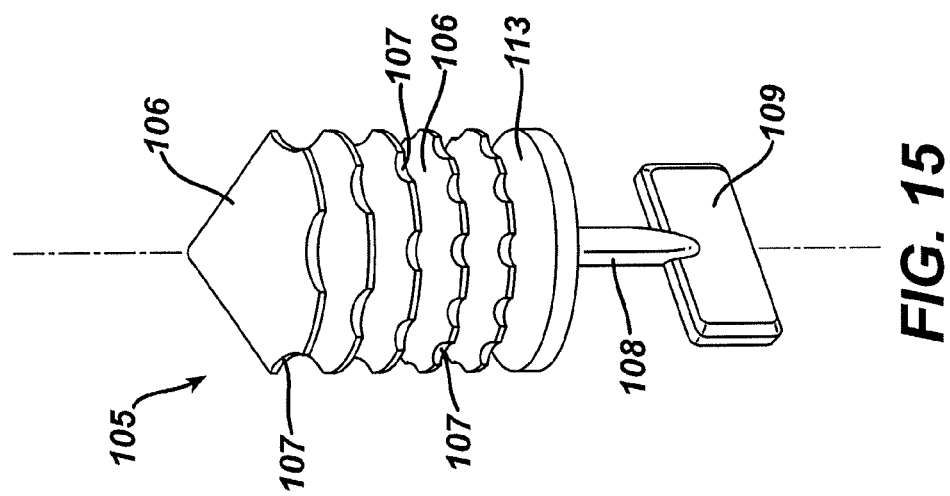
FIG. 15 depicts a perspective view of a cutting member of the morcellating device of FIG. 14.
Figure 14:
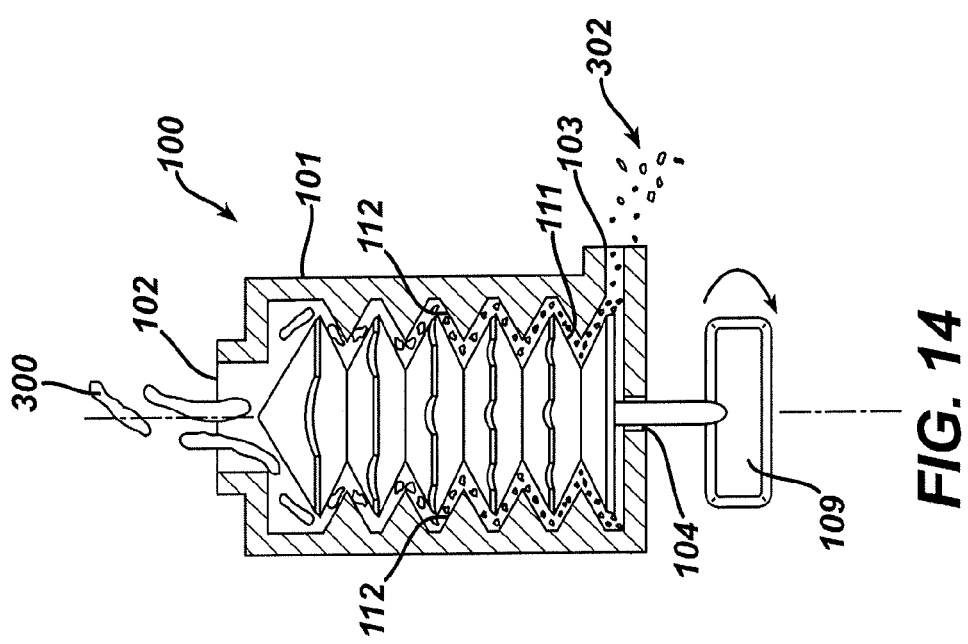
FIG. 14 depicts a side cross-sectional view of another exemplary tissue morcellating device.

FIGS. 14-16 depict yet another exemplary morcellating apparatus (100), which comprises a housing (101) defining a tubular morcellating chamber therein, and a cutting member (105) rotatably positioned within the morcellating chamber. As best seen in FIG. 15, cutting member (105) of this example generally comprises a series of cutting discs (106) mounted on top of one another such that each cutting disc (106) is aligned along a common longitudinal axis. A shaft (108) extends away from the lowermost cutting disc (106). A handle (109) is attached to the other end of shaft (108) in order to facilitate manual rotation of cutting member (105). As shown in FIG. 14, cutting member (105) is disposed within housing (101). Housing (101) includes a central aperture (104) through which shaft (108) extends, such that the longitudinal axis of shaft (108) is aligned with the longitudinal axis of the morcellating chamber of housing (101). In some versions, a seal or gasket (not shown) is positioned within central aperture (104) about shaft (108), substantially preventing leakage of tissue and/or liquids along shaft (108). Such a seal or gasket may be configured to permit cutting member (105) (including shaft (108), etc.) to be rotated relative to housing (101).

Each cutting disc (106) has a generally circular outer circumference, and in the example shown each cutting disc (106) has the same diameter. If desired, the diameter of cutting discs (106) may vary (e.g., in order to facilitate tissue cutting and/or downstream movement of the tissue specimens, etc.). The top portion of each cutting disc (106) in the present example has a generally frustoconical shape, including an angled upper surface (110). Similarly, the bottom portion of each cutting disc (106) in the present example has a generally frustoconical shape, including an angled lower surface (111). Of course, upper surface (110) and/or lower surface (111) may alternatively be substantially flat, such that cutting discs (106) have substantially flat disc shapes. In the present example, the uppermost cutting disc (106) (i.e., the cutting disc (106) nearest inlet (102) in housing (101)) has a conical upper surface in order to guide tissue specimens toward outlet (103) during use. Also, in the present example, the lower surface (111) of the lowermost cutting disc (106) is substantially flat. In some versions, such a configuration may prevent over-dicing of tissue particles. It should also be understood that, in some versions, such a configuration may facilitate tissue particle egress. Of course, the configuration of each cutting disc (106) may be varied in numerous other ways and the interior of housing (101) may be altered to cooperate with any of a variety of configurations for cutting discs (106).

Housing (101) includes an inlet (102) formed at one end and an outlet (103) formed at another end. Tissue specimens (300) may be introduced into housing (101) through inlet (102), and the morcellated or minced tissue pieces (302) may be removed or expelled from housing (101) through outlet (103). Tissue specimens (300) may be manually placed into housing (101), or supplied via an entrainment medium (e.g., air, saline, or other fluid, etc.) under pressure such that the morcellated or minced tissue (302) is expelled from the apparatus through outlet (103). Housing (101) also includes a plurality of grooves (112) which extend around the interior circumference of housing (101). Circumferential grooves (112) are located, sized and configured such that cutting member (105) may be matingly, and rotatably positioned within housing (101). In the present example, grooves (112) have a generally V-shaped cross-section that corresponds to the upper and lower surfaces (110, 111) of cutting members (106).

In order to cut tissue specimens (300) urged through housing (101) toward outlet (103) and to allow the tissue specimens (300) to travel through morcellating apparatus (100), each cutting disc (106) also includes a plurality of inwardly-extending notches (107) located about the periphery of cutting disc (106). Notches (107) extend inwardly from the outer circumference of each cutting disc (106), and may be provided in any of a variety of shapes. In the present example, notches (107) each have a generally arcuate shape (e.g., hemi-circular or hemi-elliptical) shape. Of course, any other suitable shape or combination of shapes may be used. At least a portion of each notch (107) may also be sharpened in order to facilitate tissue cutting. As also shown in FIG. 15, notches (107) may be provided in progressively smaller sizes such that notches (107) on the uppermost cutting discs (106) (e.g., those nearest inlet (102)) are the largest; and notches (107) on the lowermost cutting discs (106) (e.g., those nearest outlet (103)) are the smallest. Similarly, the number of notches (107) per cutting disc (106) may increase as the size of notches (107) decreases, such that the number of notches (107) per cutting disc (106) increases from inlet (102) toward outlet (103). In some versions, the angular positions of notches (107) on a given cutting disc (106) are also staggered relative to the angular positions of notches (107) on adjacent cutting discs (106). In the present example, the lowermost disc (113) lacks any notches (107). The absence of notches (107) on lowermost disc (113) may facilitate expulsion of morcellated or minced tissue pieces (302) toward and through outlet (103). Of course, lowermost disc (113) may include notches (107) if desired.

During an exemplary use of morcellating apparatus (100), tissue specimens (300) may be introduced into housing (101) through inlet (102) (e.g., by being entrained in pressurized air, saline, or other fluid, etc.). Cutting member (105) is then rotated, either manually using handle (109), or using a motor or other type of actuator. As cutting member (105) is rotated, cutting discs (106) will also rotate. The tissue specimens (300) will pass through cutting notches (107) in uppermost (i.e., the most upstream) cutting disc (106). As they pass into notches (107), the rotation of cutting disc (106) will cause the sharpened edges of notches (107) to cut the tissue specimens (300) into smaller pieces. As each tissue specimen (300) moves downstream through morcellating apparatus (100), the progressively smaller cutting notches (107) will cut the specimens (300) into even smaller pieces. The morcellated tissue pieces (302) are then expelled through outlet (103). The resulting morcellated or minced tissue (302) may then be processed and used in a medical fluid mixture as described herein and/or accordance with the above teachings of any of the patents or patent publications cited herein; or in any other suitable fashion.

It should be understood that cutting member (105) may be either rotated in just one direction or rotated in both directions (e.g., in a rocking action) in order to morcellate or mince tissue specimens (300). It should also be understood that, while handle (109) is rotated manually by a user to rotate cutting member (105) in the present example, cutting member (105) may alternatively be rotated by a motor or other device. Furthermore, morcellating apparatus (100) may be either provided as a stand-alone device or as a component of a tissue harvesting device. For instance, as with other morcellating apparatuses (10, 20, 30, 40, 60, 80) described herein, morcellating apparatus (100) may be provided as morcellating apparatus (240) of tissue harvesting and morcellating device (200) described above. Other suitable features, configurations, uses, and contexts for morcellating apparatus (100) will be apparent to those of ordinary skill in the art in view of the teachings herein.

Figure 17:
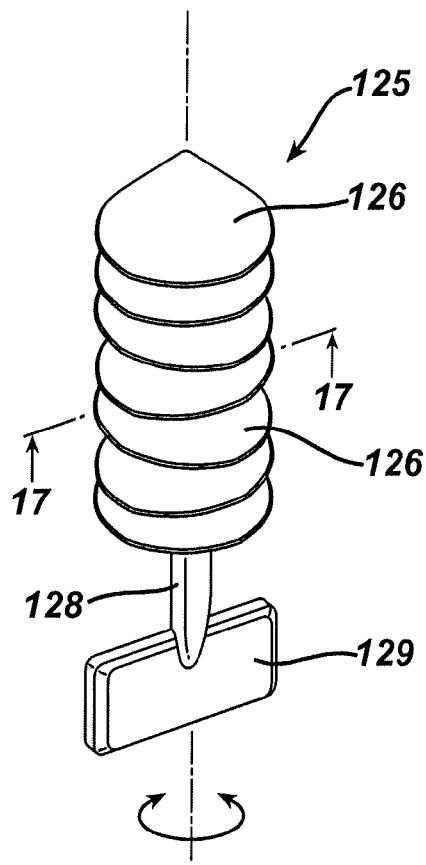
FIG. 17 depicts a perspective view of an exemplary alternative cutting member usable with the morcellating device of FIG. 14.
Figure 18:
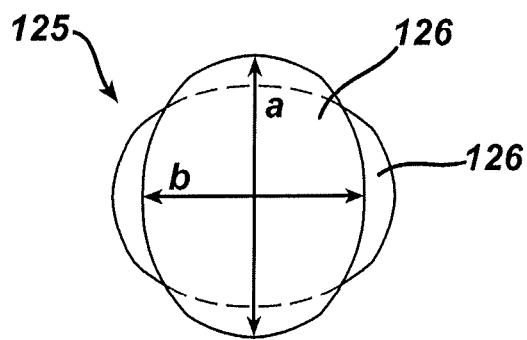
FIG. 18 depicts a top plan view of the cutting member of FIG. 17.

FIGS. 17-18 depict an exemplary modified cutting member (125) that may be used in morcellating apparatus (100) in place of cutting member (105). Cutting member (125) of this example has a plurality of cutting discs (126) mounted on top of one another such that each cutting disc (126) is aligned along a common longitudinal axis. A shaft (128) extends away from the lowermost cutting disc (126). A handle (129) is attached to the other end of shaft (128) in order to facilitate manual rotation of cutting member (125). In the present example, cutting discs (126) do not include cutting notches (although they may be included, if desired). Cutting discs (126) of this example have an elliptical or ovular outer circumference rather than a circular outer circumference. In particular, each cutting disc (126) has a major (or maximum) diameter (designated as "a" in FIG. 18), which is slightly less than the inner diameter of housing (101), and at least one minor diameter (designated as "b" in FIG. 18) which is smaller than the major diameter. In this manner, when cutting member (125) is positioned within housing (101), a pair of crescent-shaped passageways will be present between the outer circumference of each cutting disc (126) and the interior wall of housing (101), on opposite sides of each cutting disc (126). Like cutting discs (106) described above, cutting discs (126) of the present example are configured to cooperate with grooves (112) in housing (101) to morcellate or mince tissue specimens as cutting member (125) is rotated relative to housing (101). Alternatively, cutting member (125) may be used with a variation of housing (101) where the inner walls of the mincing chamber are substantially straight and do not have grooves (112). In such versions, cutting discs (126) may still cooperate with the inner sidewall of housing (101) to morcellate or mince tissue specimens as cutting member (125) is rotated relative to housing (101). The outer circumferential edge of each cutting disc (106) may also be sharpened in order to facilitate cutting.

As can also be seen in FIG. 18, each cutting disc (126) is angularly offset from each adjacent cutting disc (126). In particular, each cutting disc (126) is angularly offset from each adjacent cutting disc (126) by approximately 90°, such that the major axis of each cutting disc (126) is substantially perpendicular to the major axis of teach adjacent cutting disc (126). Of course, cutting discs (126) need not necessarily be offset in this way in every version. Indeed, cutting discs (126) may be oriented and arranged in any other suitable fashion and adjacent cutting discs (126) may have any other suitable relationships with each other. In some versions, cutting discs (126) are substantially elevationally parallel with each other, despite being angularly offset from each other. In some other versions, cutting discs (126) are elevationally tilted relative to each other. Such a tilted relationship may be provided in addition to or in lieu of cutting discs (126) being angularly offset from each other. In some versions, cutting discs (126) comprise substantially flat discs, such that the upper and lower surfaces of each cutting disc (126) are substantially flat. Alternatively, the top and/or bottom surfaces of cutting discs (126) may be angled, such that at least part of each cutting disc (126) has a frustoconical shape. Still other suitable configurations, positions, orientations, and relationships for cutting discs (126) will be apparent to those of ordinary skill in the art in view of the teachings herein.

During an exemplary use of cutting member (125) in housing (101), tissue specimens (300) may be introduced into housing (101) through inlet (102) (e.g., by being entrained in pressurized air, saline, or other fluid, etc.). In the present example, the uppermost cutting disc (126) has a conical upper surface, which may facilitate guidance of tissue specimens (300) into the space between the outer edges of cutting discs (126) and the inner wall of the morcellating chamber of housing (101). Cutting member (125) is rotated, either manually using handle (129) or using a motor or other type of actuator, as tissue specimens (300) move through housing (121) toward outlet (103). As cutting member (125), and hence cutting discs (126), rotates, a tissue specimen (300) passing between the outer edge of a cutting disc (126) and the inner wall of housing (101) will be cut by the rotating outer edge of cutting disc (126). Tissue specimens (300) will be cut into smaller and smaller pieces (302) as they travel through housing (101) toward outlet (103). The morcellated tissue pieces (302) are then expelled through outlet (103). The resulting morcellated or minced tissue (302) may then be processed and used in a medical fluid mixture as described herein and/or accordance with the above teachings of any of the patents or patent publications cited herein; or in any other suitable fashion.

It should be understood that cutting member (125) may be either rotated in just one direction or rotated in both directions (e.g., in a rocking action) in order to morcellate or mince tissue specimens (300). It should also be understood that, while handle (129) is rotated manually by a user to rotate cutting member (125) in the present example, cutting member (125) may alternatively be rotated by a motor or other device. Furthermore, a morcellating apparatus having cutting member (125) may be either provided as a stand-alone device or as a component of a tissue harvesting device. For instance, as with other morcellating apparatuses (10, 20, 30, 40, 60, 80, 100) described herein, such a morcellating apparatus may be provided as morcellating apparatus (240) of tissue harvesting and morcellating device (200) described above. Other suitable features, configurations, uses, and contexts for a morcellating apparatus having cutting member (125) will be apparent to those of ordinary skill in the art in view of the teachings herein.

VI. Miscellaneous

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Versions of the devices described above may be actuated mechanically or electromechanically (e.g., using one or more electrical motors, solenoids, etc.). However, other actuation modes may be suitable as well including but not limited to pneumatic and/or hydraulic actuation, etc. Various suitable ways in which such alternative forms of actuation may be provided in a device as described above will be apparent to those of ordinary skill in the art in view of the teachings herein.

Versions of the devices described above may have various types of construction. By way of example only, any of the devices described herein, or components thereof, may be constructed from suitable metals, ceramics, plastics, or combinations thereof. Furthermore, although not required, the construction of devices described herein may be configured to be compatible with or optimize their use with various imaging technologies. For instance, a device configured for use with MRI may be constructed from all non-ferromagnetic materials. Also for instance, when using optional imaging technologies with devices described herein, certain configurations may include modifications to materials of construction such that portions or the device may readily appear in a resultant image. Various suitable ways in which these and other modifications to the construction of devices described herein may be carried out will be apparent to those of ordinary skill in the art in view of the teachings herein.

Versions of the devices described above may have application in conventional medical treatments and procedures conducted by a medical professional, as well as application in robotic-assisted medical treatments and procedures.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for morcellating soft tissue specimens obtained from a patient, the apparatus comprising:
    (a) a housing having a morcellating chamber extending axially from a first end of the housing to a second end of the housing, the housing being configured to allow soft tissue specimens to be urged axially through the morcellating chamber;
    (b) a first tissue cutting screen comprising a plurality of elongate cutting members arranged such that tissue passageways are provided between adjacent cutting members, wherein the plurality of elongate cutting members are configured in a grid pattern such as to form a wire mesh, the first tissue cutting screen being mounted within the housing such that the elongate cutting members extend transversely across at least a portion of the morcellating chamber;
    wherein the first tissue cutting screen is rotatable within the housing;

wherein the first tissue cutting screen is mounted within the housing such that soft tissue specimens urged axially through the morcellating chamber pass through the first tissue cutting screen such that the tissue specimens are cut into smaller pieces by the cutting members; and (c) a second tissue cutting screen comprising a plurality of elongate cutting members arranged such that tissue passageways are provided between adjacent cutting members of the second tissue cutting screen, wherein the second tissue cutting screen is fixedly mounted within the housing in a spaced-apart relationship to the first cutting screen with the elongate cutting members of the second screen extending transversely across at least a portion of the morcellating chamber.

2. The apparatus of claim 1, wherein the first tissue cutting screen further comprises a frame having a central opening therein, wherein the elongate cutting members extend across the central opening, wherein the first tissue cutting screen is mounted within the housing such that the central opening extends transversely across the morcellating chamber.

3. The apparatus of claim 2, wherein the elongate cutting members comprise a plurality of wire members extending across the central opening in a grid pattern.

4. The apparatus of claim 1, wherein the first tissue cutting screen is mounted within the housing downstream of the second tissue cutting screen so as to further cut tissue specimens into smaller pieces.

5. The apparatus of claim 4, wherein the elongate cutting members of the first and second tissue cutting screens comprise a plurality of wire members extending transversely across the morcellating chamber in first and second grid patterns, respectively, and wherein the wire members of the first tissue cutting screen are spaced more closely to one another than the wire members of the second tissue cutting screen.

6. The apparatus of claim 5, wherein the second tissue cutting screen further comprises a frame having a central opening therein, wherein the elongate cutting members extend across the central opening, wherein the first tissue cutting screen is mounted within the housing such that the central opening extends transversely across the morcellating chamber, wherein the outer circumference of the frame of the first tissue cutting screen comprises a gear, and wherein the actuator comprises a drive gear meshed with the gear on the frame of the first tissue cutting screen.

7. The apparatus of claim 6, wherein the drive gear comprises a bevel gear.

* * * * *